(12) United States Patent
Drake et al.

(10) Patent No.: US 7,745,635 B1
(45) Date of Patent: Jun. 29, 2010

(54) ENERGETIC IONIC SALTS

(76) Inventors: Greg W. Drake, 40222 Peonza La., Palmdale, CA (US) 93551; Tommy Hawkins, 2521 Lawrence Ave., Lancaster, CA (US) 93536; Kerri Tollison, 2629 W. Milling St., Lancaster, CA (US) 93536

( * ) Notice: Subject to any disclaimer, the term of this patent is extended or adjusted under 35 U.S.C. 154(b) by 2095 days.

(21) Appl. No.: 10/465,836

(22) Filed: Jun. 16, 2003

(51) Int. Cl.
*C07D 249/08* (2006.01)
*C06B 25/34* (2006.01)

(52) U.S. Cl. ................................. 548/265.6; 149/92
(58) Field of Classification Search ............. 548/265.6; 149/92
See application file for complete search history.

(56) References Cited

U.S. PATENT DOCUMENTS

| | | | |
|---|---|---|---|
| 4,602,944 A * | 7/1986 | West | 504/257 |
| 5,840,894 A * | 11/1998 | Schneider et al. | 544/350 |
| 6,504,033 B1 * | 1/2003 | Bourdauducq | 548/265.6 |
| 6,509,473 B1 * | 1/2003 | Drake | 548/262.2 |
| 7,550,601 B1 * | 6/2009 | Drake et al. | 548/255 |
| 7,645,883 B1 * | 1/2010 | Hawkins et al. | 548/255 |

FOREIGN PATENT DOCUMENTS

| | | | |
|---|---|---|---|
| EP | 142248 | * | 5/1985 |
| JP | 51-16671 | * | 2/1976 |

OTHER PUBLICATIONS

English translation of JP 51-16671.*
Astleford et al., Journal of Organic Chemistry, 54, 731-732, 1989.*
Tamura et al., Chemical Abstracts, 86:89703, 1977.*
West, Chemical Abstracts, 103:178174, 1985.*
Panasenko, Chemical Abstracts, 141:271254, 2004.*

* cited by examiner

*Primary Examiner*—Fiona T Powers
(74) *Attorney, Agent, or Firm*—AFMCLO/JAZ; William J. O'Brien

(57) ABSTRACT

The invention provides a) a method for making improved ionic halide salts, e.g., 1-methyl-4-amino-1,2,4-triazolium iodide and b) a method for making energetic ionic salts, e.g., 1-methyl-4-amino-1,2,4-triazolium nitrate, in high yield and purity from triazolium precursors. Also provided are the resulting novel salts from the above methods.

5 Claims, No Drawings

ENERGETIC IONIC SALTS

STATEMENT OF GOVERNMENT INTEREST

The invention described herein may be manufactured and used by or for the Government for governmental purposes without the payment of any royalty thereon.

RELATED APPLICATIONS

Patent application Ser. No. 09/688,909, entitled *Energetic Triazolium Salts* by Greg W. Drake, inventor, filed on 16 Oct. 2000.

FIELD OF THE INVENTION

This invention relates to energetic ionic salts and methods for preparing same.

BACKGROUND OF THE INVENTION

Prominent in the field of monopropellants in hydrazine, a highly toxic material, for which a replacement is being sought. Hydrazine's largest inherent drawback, is its considerable vapor pressure at ambient temperature of approximately 12-14 torr, which leads to a high vapor toxicity. This results in high handling and transfer costs in its use in satellite control devices. A current branch of research of the USAF, is the synthesis and use of new low melting energetic salts either alone or as mixtures with other well-known energetic materials, as new monopropellant materials. These salts offer several inherent advantages over materials such as hydrazine and high concentration hydrogen peroxide, including negligible vapor pressure and significantly improved densities. These properties should make these new materials very appealing to space missions for both government and private interests.

The search for new energetic materials having applications as monopropellant ingredients and/or new fuels is an ongoing research endeavor. Much effort has been applied to find new low melting salts having many inherent advantages over neutral materials such as hydrazine. These advantages include negligible vapor pressure at working conditions as well as much improved densities, usually on the order of 50% or greater. These advantages become apparent in the handling, storage, and lifetime of the device employing the propellant material.

Ionic liquids are known and discussed in two recent patent applications, U.S. Patent Application Publication #2002/0015883 entitled "Ionic liquids" by Hilarius et al, dated Feb. 7, 2002 and Schmidt et al, U.S. Patent Application Publication #2002/0015884 entitled "Ionic liquids II", dated Feb. 7, 2002. However, none of these references have the newly claimed ionic liquid salts of the present invention as disclosed below nor do they make claims for new energetic materials or new fuels for their systems.

Accordingly, there is need and market for energetic materials of minimized vapor toxicity that overcome the above prior art shortcomings.

There has now been discovered energetic compositions of low vapor toxicity with enhanced stability and performance and method for making same.

SUMMARY OF THE INVENTION

Broadly the invention provides a) a method for making improved ionic halide salts and b) a method for making energetic ionic salts in high yield and purity from precursor ionic halide salts as more fully discussed below. Also provided are the resulting novel salts from the above methods.

The synthesis of newly invented 1-substituted-4-amino-1, 2,4-triazolium energetic salts is described as follows. A large family of energetic salts has been synthesized in high yield and high purity using commonly available starting materials. The reaction of 4-amino-1,2,4-triazole with alkyl halides in polar aprotic solvents yields 1-substituted-4-amino-1,2,4-triazolium halide salts. This reaction is not novel, it was described for the synthesis of several 1-n-alkyl-4-amino-1,2, 4-triazolium halides by Scriven, Keay, Goe, and Astleford (*J. Org. Chem.* 1989, 54, 731). However, in their synthesis, they generally used only one equivalent of n-alkyl halide to one equivalent of 4-amino-1,2,4-triazole.

However, it has been found that if the experiment is run with excess alkyl halide, n>2, most desirable 2-4 mole equivalents, the 1-substituted-4-amino-1,2,4-triazolium halide salt can be recovered in essentially quantitative yield, usually as highly crystalline substances, with no contamination with 4-amino-1,2,4-triazole. (Reaction 1)

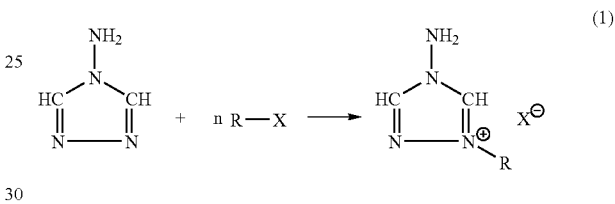

(1)

In this case R can be but not limited to either straight, branched, cyclic, unsaturated i.e. double or triple bonds in a hydrocarbon chain of carbon atoms from $C_1$-$C_{20}$. This chain can also contain heterotoms including nitrogen (functional groups include amines (R,R'N—), (—N(R')—) or (—NH$_2$) and their corresponding protonated forms, amides (—N—C(=O)—), urethanes (—N—C(=O)—N(R)—), and substituted guanidines (N(R)—C(=NR")—N(R') whereby R, R', and R" may or may equal and can be a hydrogen, amine, alkyl chain branched, straight, oxygen within the chain such as an ether linkage (—O—), ester (—O—C(=O)—), alcohol (—OH) or carbonyl (—C(=O)—) or terminal on the chain or as a pendant group. As for the X in the R—X, it can be any typical leaving group, i.e. a group that can be easily displaced by a nucleophilic center and are commonly used by those skilled in the art, where X can be represented by but not limited to bromine, chlorine, iodine, substituted sulfate —S(=O)$_2$—R where R can be an alkyl, phenyl, substituted phenyl, trifluoromethyl (—S(=O)$_2$—CF$_3$), and nitratato —ONO$_2$.

Through the simple reaction of the 4-amino-1,2,4-triazolium salt with an appropriate salt of an energetic anion in polar solvents such as low molecular weight alcohol, the X-paired anion of the substituted 4-amino-1,2,4-triazolium salt is replaced with a desirable energetic anion, whereby the unwanted metathetical product is easily removed by filtration. (Reaction 2)

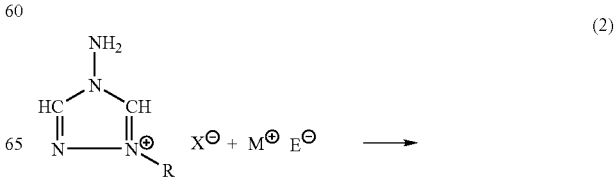

(2)

-continued

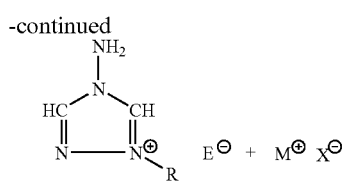

Typically the M+ cation can be but is not limited to silver (Ag+), potassium (K+), sodium (Na+), Strontium (Sr+), cesium (Cs+), ammonium (NH$_4^+$) substituted ammonium NRR'R"R'"+ (where R, R', R", R'" can be equivalent or all different with some but not all pendant R groups being hydrogen atoms, while R, R', R", and R'" can be simple alkyl chains from $C_1$-$C_{20}$ and these substituted R groups can be straight, branched, cyclic, unsaturated or joined together as well as the chains containing other heteroatoms such as nitrogen or oxygen. Similarly, the substituted ammonium cations can be attached to a polymer backbone as represented by the well known class of ion exchange resins such as the commercially available DOWEX™ resins.

As for the E– anion, those skilled in the art will realize that any anion which carries a relatively high oxygen content and or high nitrogen content and/or having a high heat of formation including but not limited to nitrate ($NO_3^-$), perchlorate ($ClO_{4-}$), dinitramide ($N(NO_2)_2^-$), nitroformate ($C(NO_2)_3^-$), nitrocyanamide $N(NO_2)(CN)^-$, dicyanamide ($N(CN)_2^-$), 5-nitro-1,2,3,4-tetrazoloate, 3-nitro-1,2,4-triazolate, 3,5-dinitro-1,2,4-triazolate, 2,4,5-trinitro-1,3-imidazolate, bitetrazolate, bitetrazolylamide, perchlorylamide(N—$ClO_3^{-2}$), 2-oxo-5-nitro-1,2,3,4-tetrazolate, and 1-oxo-3,5-dinitro-1,2,4-triazolate.

For those skilled in the art, it will be realized that the reactions will be carried out best in polar solvent systems due to the solubility and nature of the reagents. What is meant by polar solvents are solvents that have a natural dipole and a reasonable dielectric constant and can dissolve like materials. Examples include but are not limited to acetonitrile lower weight alcohols such as methanol, ethanol, n-propanol, isopropanol and n-butanol, nitromethane, cyanothane, dimethylsulfoxide, and mixtures thereof.

Thus, a new family of low melting salts called ionic salts or liquids has been uncovered and their synthesis routes are facile, high yield and lead to high purity products made from readily available materials with simple experimental means. The salts of the invention preferably melt below 100° C. and thus are ionic liquids.

These new energetic salts have relatively low melting points yet still have long liquid ranges before decomposition. All of the product salts are soluble in polar solvents such as isopropanol, methanol, ethanol, acetonitrile, as well as water. They are new members of the well known class of materials described as ionic liquids. These materials have several inherent advantages over conventional energetic materials. The new materials being salts have no vapor pressure at ambient temperatures, results in enhanced safety properties, most notable being lessened toxicity and highly reduced flammability. As new propellant materials, they can serve as energetic ingredients in monopropellants or as new fuels in bipropellant scenarios. In the case where the new salts might be used as a fuel, they have several inherent advantages over conventional fuels. They have densities ranging from 1.30 g/cm$^3$ to almost 1.60 g/cm$^3$, which are from 60 to 100% greater than hydrocarbon based materials. Secondly, the materials have essentially no vapor pressure, which leads to much easier handling and significantly lowered flammability. These properties make these new materials much more attractive as new fuels and/or monopropellant ingredients.

The following Examples serve to illustrate the invention but should not be construed in limitation thereof.

EXAMPLE 1

1-ethanol-4-amino-1,2,4-triazolium nitrate

In a 125 ml Erlenmeyer flask, 0.6690 g, 3.2 mmoles of 1-ethanol-4-amino-1,2,4-triazolium bromide was dissolved in 25 ml of fresh methanol and stirred vigorously. Silver nitrate, 0.5420 grams, 3.2 mmoles, was dissolved in 20 ml of fresh methanol along with 2 ml of acetonitrile in a separate flask. The silver nitrate alcohol solution was then added slowly to the vigorously stirred solution of 1-ethanol-4-amino-1,2,4-triazolium bromide. The silver nitrate flask was washed with three, five ml quantities of methanol, and subsequently transferred to the reaction solution. The reaction was allowed to stir an additional 45 minutes in the dark at ambient temperature. The silver bromide was then filtered away and was washed with two, ten ml quantities of fresh methanol. The filtrate and washings were rotoevaporated down to leave a viscous oil. The oil was then transferred to a preweighed flask and evacuated overnight at 60° C. to leave 0.6086 grams, 3.18 mmoles of 1-ethanol-4-amino-1,2,4-triazolium nitrate in excellent purity. Melting point 0° C.; DSC onset 180° C.

$^1$H NMR (d$_6$-dmso): 3.787, 3.800, 3.812 (triplet, relative area 2.000), 4.384, 4.397, 4.409 (triplet, relative area 2.023), 6.95 (broad, relative area 3.103), 9.208 (singlet, relative area 0.832), 10.190 (singlet, relative area 0.891).

$^{13}$C NMR (d$_6$-dmso): 54.880 (singlet), 58.159 (singlet), 143.096 (singlet), 145.524 (singlet).

EXAMPLE 2

1-ethanol-4-amino-1,2,4-triazolium bromide 5.000 grams, 59.4 mmoles of 4-amino-1,2,4-triazole was dissolved in 200 ml of fresh acetonitrile and stirred vigorously. 29.800 grams of 2-bromoethanol was added slowly to the solution by pipet. After the addition was complete, the reaction mixture was heated for 20 hours at 80° C., until thin layer chromatography revealed that all of the 4-amino-1,2,4-triazole had been consumed. The reaction mixture was then allowed to cool to room temperature and then was rotary evaporated down to leave a viscous oil. Hot isopropyl alcohol was added to the oil dissolving it. Storage of the resultant solution in a refrigerator resulting in a large crop of a viscous oil of 1-ethanol-4-amino-1,2,4-triazolium bromide, 9.9332 g, 47.5 mmoles. Melting point 0-5° C.; DSC onset 180° C.

$^1$H NMR (d$_4$-MeOH): 3.956, 3.962, 3.969, 3.976, 3.981 (complex triplet, relative area 2.000), 4.495, 4.500, 4.508 (triplet, relative area 2.029), 4.834 (broad singlet, relative area 3.089), 8.971 (singlet, relative area 0.845), 10.036 (singlet, relative area 0.842).

$^{13}$C NMR (d$_4$-MeOH): 56.675 (singlet), 59.813 (singlet), 144.999 (singlet), 146.911 (singlet)

EXAMPLE 3

1-n-butyl-4-amino-1,2,4-triazolium nitrate

In a 125 ml Erlenmeyer flask, 2.7721 g, 12.5 mmoles of 1-n-butyl-4-amino-1,2,4-triazolium bromide was dissolved in 30 ml of fresh methanol and stirred vigorously. Silver nitrate, 2.1290 grams, 12.5 mmoles, was dissolved in 25 ml of fresh methanol and 2 ml of acetonitrile in a separate flask. The silver alcohol solution was then added slowly to the vigorously stirred solution of 1-n-butyl-4-amino-1,2,4-triazolium bromide. The silver nitrate flask was washed with three, five ml quantities of methanol, and subsequently transferred to the reaction solution. The reaction was allowed to stir an additional 45 minutes in the dark at ambient temperature. The silver bromide was filtered away and washed with three, five ml aliquots of fresh methanol. The filtrate and washings were rotary evaporated down to leave a viscous oil. The oil was then transferred to a preweighed flask and evacuated overnight at 60° C. to leave 2.0313 grams, 10 mmoles of 1-n-butyl-4-amino-1,2,4-triazolium nitrate in excellent purity. Melting point 0° C., DSC onset 190° C.

$^1$H NMR (d$_4$-MeOH): 0.962, 0.980, 0.999 (triplet, relative area 3.000), 1.349, 1.367, 1.386, 1.405, 1.424, 1.442 (sextet, relative area 1.992), 1.906, 1.925, 1.943, 1.962, 1.980 (pentet, relative area 2.076) 4.392, 4.410, 4.428 (triplet, relative area 1.978), 4.807 (broad, relative area 1.858), 8.918 (singlet, relative area 0.849), 10.044 (singlet, relative area 0.802).

$^{13}$C NMR (d$_4$-MeOH): 13.885 (singlet), 20.447 (singlet), 31.796 (singlet), 53.792 (singlet), 144.505 (singlet), 146.827, (singlet).

EXAMPLE 4

1-(2-sulfatoethyl)-4-amino-1,2,4-triazole 1,2-O,O'-sulfatoethane (Aldrich), 0.9836 g, 7.92 mmoles and 4-amino-1,2,4-triazole, 0.6663 g, 7.91 mmoles were placed in a 100 ml round bottom flask. Acetonitrile, 25 ml was added along with a Teflon stir bar and the reaction mixture was stirred vigorously at room temperature. There was an immediate reaction with the formation of a white precipitate. The reaction was stirred for 2 hours at room temperature, whereupon it was filtered, and the white solid was collected and washed with fresh actonitrile, three 10 ml aliquots, followed by washing with three 10 ml aliquots of diethyl ether. The solid was then transferred to a preweighed flask and vacuum dried to a constant mass, yielding 1.5358 grams, 7.3 mmoles of 1-(2-sulfatoethyl)-4-amino-1,2,4-triazole inner salt.

$^1$H NMR (d$_6$-dmso): 4.155, 4.168, 4.180, 4.567, 4.580, 4.591 (two triplets in close proximity, relative area 4.583), 7.001 (broad, relative area 1.603), 9.189 (singlet, relative area 0.963), 10.116 (singlet, relative area 1.000).

$^{13}$C NMR (d$_6$-dmso): 52.105 (singlet), 62.793 (singlet), 143.111 (singlet), 145.249 (singlet).

EXAMPLE 5

1-n-butyl-4-amino-1,2,4-triazolium perchlorate

In a 125 ml Erlenmeyer flask, 2.163 g, 9.78 mmoles of 1-n-butyl-4-amino-1,2,4-triazolium bromide was dissolved in 30 ml of fresh methanol and stirred vigorously. Silver nitrate, 2.021 grams, 9.74 mmoles, was dissolved in 15 ml of fresh methanol in a separate flask. The silver perchlorate alcohol solution was then added slowly to the vigorously stirred solution of 1-n-butyl-4-amino-1,2,4-triazolium bromide. The silver perchlorate flask was washed with three, five ml quantities of methanol, and subsequently transferred to the reaction solution. The reaction was allowed to stir an additional 45 minutes in the dark at ambient temperature. The silver bromide was filtered away through a celite plug and subsequently washed with three, five ml quantities of fresh methanol. The filtrate and washings were rotary evaporated down to leave a viscous oil. The oil was then transferred to a preweighed flask and evacuated overnight at 60° C. to leave 2.2737 grams, 9.44 mmoles of 1-n-butyl-4-amino-1,2,4-triazolium perchlorate in excellent purity. Melting point 0° C., DSC onset 250° C.

$^1$H NMR (d$_4$-MeOH): 0.808, 0.863, 0.881, 0.899 (quartet, relative area 3.000), 1.264, 1.283, 1.302, 1.321, 1.339, 1.357 (sextet, relative area 2.028), 1.813, 1.833, 1.851, 1.854, 1.863, 1.869, 1.871, 1.888 (complex multiplet, relative area 2.027), 4.337, 4.295, 4.313 (triplet, relative area 2.001), 4.665 (broad singlet, relative area 1.667), 8.726 (singlet, relative area 0.947), 9.710 (singlet, relative area 0.970).

$^{13}$C NMR (d$_4$-MeOH): 13.782, singlet, 20.314, singlet, 31.634, singlet, 53.706, singlet, 144.384, singlet, 146.691, singlet.

EXAMPLE 6

1-propyl-4-amino-1,2,4-triazolium bromide 10.005 g 118 mmoles of 4-amino-1,2,4-triazole was weighed out and transferred to a three necked 500 ml, round bottom flask and dissolved 200 ml of acetonitrile. The solution then was stirred vigorously with an overhead stirrer the flask equipped with a reflux condenser and placed in a hot oil bath (50° C.) and allowed to heat. In a graduated cylinder, 1-bromopropane 58.865 g, 478 mmoles, was weighed out and then was slowly added to the hot 4-amino-1,2,4-triazole/acetonitrile mixture. The reaction mixture was stirred with heating for 36 hours, being monitored by thin layer chromatography, at which time the 4-amino-1,2,4-triazole was consumed. The flask was then removed from the oil bath, cooled under nitrogen atmosphere. The reaction solution was transferred to a large round bottomed flask and the acetonitrile and excess n-propyl bromide rotary evaporated away. The resultant oil was transferred to a preweighed Schlenk flask, rinsing the large flask with three 10 ml aliquots of fresh acetonitrile. The flask was evacuated for 20 hours to yield a highly crystalline solid 23.9584 g, 115 mmoles of 1-n-propyl-4-amino-1,2,4-triazolium bromide. Melting point: 63° C.; DSC onset 145° C., $^1$H NMR (d$_6$-dmso): 0.806, 0.823, 0.836 (triplet, relative area 3.000), 1.818, 1.834 (broad multiplet, relative area 2.013), 4.362, 4.373 (broad multiplet, relative area 1.999), 7.126 (broad singlet, relative area 1.816), 9.244 (singlet, relative area 0.928), 10.440 (singlet, relative area 0.957).

$^{13}$C NMR (d$_4$-MeOH): 11.051 (singlet), 23.313 (singlet), 55.538 (singlet), 144.586 (singlet), 146.908 (singlet).

EXAMPLE 7

1-n-propyl-4-amino-1,2,4-triazolium perchlorate

In a 125 ml Erlenmeyer flask, 2.0935 g, 10.1 mmoles of 1-n-propyl-4-amino-1,2,4-triazolium bromide was dissolved in 30 ml of fresh methanol and stirred vigorously. Silver perchlorate, 2.114 grams, 10.1 mmoles, was dissolved in 15 ml of fresh methanol in a separate flask. The silver nitrate alcohol solution was then added slowly to the vigorously stirred solution of 1-n-propyl-4-amino-1,2,4-triazolium bromide. The silver perchlorate flask was washed with three, five ml quantities of methanol, and subsequently transferred to the reaction solution. The reaction was allowed to stir an additional 20 minutes in the dark at ambient temperature. The silver bromide was filtered away and washed with three, five ml quantities of fresh methanol. The filtrate and washings were rotary evaporated down to leave a viscous oil. The oil was then transferred to a preweighed flask and evacuated overnight at 60° C. to leave 2.1415 grams, 9.5 mmoles of 1-n-propyl-4-amino-1,2,4-triazolium perchlorate is excellent purity. Melting point 0° C.; DSC onset 190° C.

$^1$H NMR ($d_4$-MeOH): 0.973, 0.991, 1.010 (triplet, relative area 3.000), 1.951, 1.969, 1.987, 2.005, 2.023, 2.041 (sextet, relative area 2.018), 4.341, 4.358, 4.376 (triplet, relative area 2.059) 4.774 (broad, relative area 1.872), 8.851 (singlet, relative area 0.791), 9.853 (singlet, relative area 0.887).

$^{13}$C NMR ($d_4$-MeOH): 10.957 (singlet), 23.222 (singlet), 55.505 (singlet), 144.527 (singlet), 146.830 (singlet).

EXAMPLE 8

1-ethyl-4-amino-1,2,4-triazolium bromide

A 500 ml round bottom flask equipped with an overhead stirrer was charged with 10.00 grams of 4-amino-1,2,4-triazole and 200 ml of acetonitrile. Ethyl bromide, 45 ml, 65.0 grams, was added to the vigorously stirred acetonitrile reaction mixture. The reaction was stirred for 8 days at ambient temperature at which time, thin layer chromatography showed that all of the 4-amino-1,2,4-triazole had been consumed. The resultant solution was then rotary evaporated down to leave a colorless oil which slowly crystallized. Solid material was heated to 60 C. for 5 hours under high vacuum, whereupon it melted and lost the remaining solvent and resolidified. Crystalline 1-ethyl-4-amino-1,2,4-triazolium bromide was recovered in essentially quantitative yield and high purity, 22.94 g, 117 mmoles. Melting point: 63-67° C.; DSC onset: 150° C.

$^1$H NMR ($d_6$-dmso): 1.402, 1.420, 1.438 (triplet, relative area 3.000); 4.359, 4.377, 4.395, 4.413 (quartet, relative area 2.003); 7.084 (broad singlet, relative area 1.648); 9.202 (singlet, relative area 0.959); 10.325 (singlet, relative area 1.000).

$^{13}$C NMR ($d_6$-dmso): 13.768 (singlet); 47.335 (singlet); 142.289 (singlet); 145.114 (singlet).

EXAMPLE 9

1-ethanol-4-amino-1,2,4-triazolium perchlorate

In a 125 ml Erlenmeyer flask, 2.4635 g, 11.8 mmoles of 1-ethanol-4-amino-1,2,4-triazolium bromide was dissolved in 30 ml of fresh methanol and stirred vigorously. Silver perchlorate, 2.321 grams, 11.2 mmoles, was dissolved in 15 ml of fresh methanol in a separate flask. The silver perchlorate alcohol solution was then added slowly to the vigorously stirred solution of 1-n-butyl-4-amino-1,2,4-triazolium bromide. The silver perchlorate flask was washed with three, five ml quantities of methanol, and subsequently transferred to the reaction solution. The reaction was allowed to stir an additional 15 minutes in the dark at ambient temperature. The silver bromide was filtered away and washed with three, five ml quantities of fresh methanol. The filtrate and washings were rotary evaporated down to leave a viscous oil. The oil was then transferred to a preweighed flask and evacuated overnight at 60° C. to leave 2.3541 grams, 10.3 mmols of 1-ethanol-4-amino-1,2,4-triazolium perchlorate in excellent purity. Melting point 0° C., DSC onset 190° C.

$^1$H NMR ($d_4$-MeOH): 3.867, 3.879, 3.892 (triplet, relative area 2.000), 4.387, 4.400, 4.412 (triplet, relative area 2.049), 4.679 (broad, relative area 2.817), 8.792 (singlet, relative area 0.827), 9.786 (singlet, relative area 0.993).

$^{13}$C NMR ($d_4$-MeOH): 56.543 (singlet), 59.815 (singlet), 144.986 (singlet), 146.837 (singlet).

EXAMPLE 10

1-n-propyl-4-amino-1,2,4-triazolium nitrocyanamide

In a 125 ml Erlenmeyer flask, 2.353 g, 11.3 mmoles of 1-n-propyl-4-amino-1,2,4-triazolium bromide was dissolved in 50 ml of fresh acetonitrile and stirred vigorously. Silver nitrocyanamide, 2.202 grams, 11.3 mmoles, was dissolved in 20 ml of fresh methanol in a separate flask. The silver nitrocyanamide acetonitrile solution was then added slowly to the vigorously stirred solution of 1-n-propyl-4-amino-1,2,4-triazolium bromide. The silver nitrocyanamide flask was washed with three, five ml quantities of acetonitrile, and subsequently transferred to the reaction solution. The reaction was allowed to stir an additional 30 minutes in the dark at ambient temperature. The silver bromide was filtered away and washed with three, five ml quantities of fresh methanol. The filtrate and washings were rotary evaporated down to leave a viscous oil. The oil was then transferred to a preweighed flask using fresh methanol (approximately 30 ml) and evacuated overnight at 60° C. to leave 2.450 grams, 11.3 mmoles of 1-n-propyl-4-amino-1,2,4-triazolium nitrocyanamide in excellent purity. Melting point 0° C., DSC onset 190° C.

$^1$H NMR ($d_6$-dmso): 0.845, 0.863, 0.882 (triplet, relative area 3.000), 1.816, 1.834, 1.852, 1.870, 1.888, 1.906 (sextet, relative area 1.988), 4.277, 4.294, 4.311 (triplet, relative area 1.982) 6.892 (broad, relative area 1.716), 9.153 (singlet, relative area 0.915), 10.143 (singlet, relative area 0.998).

$^{13}$C NMR ($d_6$-dmso): 10.406 (singlet), 21.677 (singlet), 53.435 (singlet), 116.605 (singlet), 142.784 (singlet), 145.362 (singlet).

EXAMPLE 11

1-ethyl-4-amino-1,2,4-triazolium nitrocyanamide

In a 125 ml Erlenmeyer flask, 2.5134 g, 12.0 mmoles of 1-ethanol-4-amino-1,2,4-triazolium bromide was dissolved in 50 ml of fresh acetonitrile along with 7 ml of methanol and stirred vigorously. Silver nitrocyanamide, 2.2378 grams, 11.6 mmoles, was dissolved in 15 ml of fresh methanol in a separate flask. The silver nitrocyanamide acetonitrile solution was then added slowly to the vigorously stirred solution of 1-n-butyl-4-amino-1,2,4-triazolium bromide. The silver nitrocyanamide flask was washed with three, five ml quantities of fresh acetonitrile, and subsequently transferred to the reaction solution. The reaction was allowed to stir an additional 30 minutes in the dark at ambient temperature. At the end of this time, 100 ml of fresh methanol was added to the reaction solution. The silver me bromide was filtered away and washed with three, five ml quantities of fresh methanol. The filtrate and washings were rotary evaporated down to leave a viscous oil. The oil was then transferred to a preweighed flask and evacuated overnight at 60° C. to leave 2.5456 grams, 11.7 mmoles of 1-ethanol-4-amino-1,2,4-triazolium perchlorate in excellent purity. Melting point 0° C., DSC onset 185° C.

$^1$H NMR ($d_6$-dmso): 3.867, 3.879, 3.892 (triplet, relative area 2.000), 4.387, 4.400, 4.412 (triplet, relative area 2.049), 6.843 (broad, relative area 2.817), 9.142 (singlet, relative area 0.954) 10.109 (singlet, relative area 0.913).

$^{13}$C NMR (d$_6$-dmso): 55.053 (singlet), 58.268 (singlet), 116.712 (singlet), 143.162 (singlet), 145.379 (singlet).

EXAMPLE 12

1-ethyl-4-amino-1,2,4-triazolium nitrate

To a preweighed Erlenmeyer flask, 2.7640 g, 14.3 mmol, of 1-ethyl-4-amino-1,2,4-triazolium bromide was measured out under nitrogen conditions. Methanol, 25 ml, was added to dissolve the salt, resulting in a clear solution, homogeneous. In a second preweighed Erlenmeyer flask, 2.3390 g, 13.7 mmol, of silver nitrate was measured out. Acetonitrile, 5 ml, was added along with 25 ml of methanol to dissolve the salt, resulting in a clear, homogeneous solution. The silver nitrate solution was added, dropwise, to the 1-ethyl-4-amino-1,2,4-triazolium bromide solution, resulting in an immediate clouding and precipitation in the solution. The reaction mixture was allowed to stir at ambient temperature for thirty minutes. At the end of the thirty minutes the reaction mixture was filtered through a filter set up (large 2-piece filter apparatus with the addition of filter paper and celite) removing the silver halide. The reaction vessel was rinsed three times, 20 ml each, with fresh methanol. The solution was transferred to a 500 ml round bottom flask, rinsing three times, 25 ml each, with fresh methanol. The flask was placed on a rotary evaporator, and the solvent was removed, leaving an oil. The oil was dissolved in a minimal amount of methanol and transferred to a preweighed Schlenk flask, placed in an oil bath at 60° C., and vacuum dried for 36 hours. Yield 2.3871 grams, 13.6 mmoles. Melting point: 0-5° C.; DSC onset 185° C.

$^1$H NMR (d$_6$-dmso): 1.396, 1.411, 1.429 (triplet, relative area 3.000), 4.361, 4.379 (broad multiplet, relative area 1.903), 7.013 (broad, relative area 2.077), 9.113 (singlet, relative area 0.946); 10.197 (singlet, relative area 0.915).

$^{13}$C NMR (d$_6$-dmso): 14.035 (singlet); 47.772 (singlet); 143.508 (singlet), 145.534 (singlet).

EXAMPLE 13

1-ethyl-4-amino-1,2,4-triazolium perchlorate

To a preweighed Erlenmeyer flask, 2.889 g, 14.9 mmol, of 1-ethyl-4-amino-1,2,4-triazolium bromide was measured out under nitrogen conditions. Methanol, 25 ml, was added to dissolve the salt, resulting in a clear solution, homogeneous. In a second preweighed Erlenmeyer flask, 2.978 g, 14.3 mmol, of silver perchlorate was measured out. Acetonitrile, 5 ml, was added along with 25 ml of methanol to dissolve the salt, resulting in a clear, homogeneous solution. The silver perchlorate solution was added, dropwise, to the 1-ethyl-4-amino-1,2,4-triazolium bromide solution, resulting in an immediate clouding and precipitation in the solution. The reaction mixture was allowed to stir at ambient temperature for thirty minutes. At the end of the thirty minutes the reaction mixture was filtered through a filter set up (large 2-piece filter apparatus with the addition of filter paper and celite) removing the silver halide. The reaction vessel was rinsed three times, 20 ml each, with fresh methanol. The solution was transferred to a 500 ml round bottom flask, rinsing three times, 25 ml each, with fresh methanol. The flask was placed on a rotary evaporator, and the solvent was removed, leaving an oil. The oil was dissolved in a minimal amount of methanol and transferred to a preweighed Schlenk flask, placed in an oil bath at 60° C., and vacuum dried for 24 hours. Yield 2.7774 grams, 13.1 mmoles. Melting point: 0-5° C.; DSC onset: 195-200° C.

$^1$H NMR (d$_6$-dmso): 1.430, 1.448, 1.466 (triplet, relative area 3.000), 4.323, 4.341, 4.359, 4.378 (quartet, relative area 1.986), 6.855 (broad, relative area 1.631), 9.099 (singlet, relative area 0.998); 10.078 (singlet, relative area 1.017).

$^{13}$C NMR (d$_6$-dmso): 13.179 (singlet); 47.547 (singlet); 142.419 (singlet), 145.221 (singlet).

EXAMPLE 14

1-methylcyclopropyl-4-amino-1,2,4-triazolium bromide 4-amino-1,2,4-triazole 3.2154 g, 38.2 mmoles, was weighed out and dissolved into 100 ml of acetonitrile in three necked, round bottomed 250 ml flask equipped with an overhead stirrer. Bromomethylcyclopropane, 10.7539 g, 79.6 mmoles, was weighed out and added slowly to the vigorously stirred 4-amino-1,2,4-triazole/acetonitrile solution. Reaction mixture was heated to 50° C. for 5 days, at which time, thin layer chromatography revealed that no 4-amino-1,2,4-triazole remained. The reaction solution was then cooled, and transferred to a large round bottomed flask and the solvent and excess bromomethylcyclopropane rotary evaporated away. The oil was transferred to a preweighed Schlenk flask using a minimal amount of acetonitrile three 10 ml aliquots. The flask and its contents were evacuated for 20 hours at ambient temperature to leave a beige crystalline solid. This solid was then transferred to a 500 ml round bottom flask, and dissolved in hot isopropanol 200 ml. The flask was then placed in a refrigerator overnight to cool. The next day the solution was layered with 100 ml of diethyl ether and returned to cold storage. Upon standing, a large crop of white crystals were formed of 1-methylcyclopropyl-4-amino-1,2,4-triazolium bromide which were washed with three 50 ml aliquots of cold isopropyl alcohol and vacuum dried to a constant weight of 4.8167 g, 22 mmoles. Melting point: 61-63° C.; DSC onset: 150-155° C.

$^1$H NMR (d$_6$-dmso): 0.461, 0.472, 0.557, 0.576 (complex multiplet, relative area 4.000), 1.27, 1.283, 1.293, 1.302, 1.313, 1.320, 1.332 (complex multiplet, relative area 0.992), 4.261, 4.279 (doublet, relative area 2.032), 7.088 (broad singlet, relative area 1.309), 9.231 (singlet, relative area 0.971), 10.412 (singlet, relative area 1.309).

$^{13}$C NMR (d$_6$-dmso): 3.849 (singlet), 10.082 (singlet), 56.162 (singlet) 142.150 (singlet), 145.179 (singlet).

EXAMPLE 15

1-methyl-4-amino-1,2,4-triazolium iodide 4-amino-1,2,4-triazole 5.1833 g, 61.6 mmoles was weighed out and placed in a 250 ml round bottom flask with a Teflon stir bar. Isopropyl alcohol, 200 ml, was added and the mixture stirred for a short period of time to completely dissolve the 4-amino-1,2,4-triazole. Methyl iodide, 26.5143 g, 186 mmoles, was then added to the vigorously stirred solution. The flask was then protected from light with a black bag, and stirred for seven days at ambient temperature. At the end of this time an additional 1.50 g of methyl iodide was added and the reaction mixture stirred for five additional days. The solution was pale yellow with white precipitate in the bottom of the flask. The precipitate was filtered and washed four aliquots, 50 ml each, of cold isopropyl alcohol, followed by four washings, 50 ml each, of cold diethyl ether. The white powder was then transferred to a preweighed Schlenk flask and evacuated overnight to leave 10.1840 g, 45 mmoles of 1-methyl-4-amino-1,2,4-triazolium iodide. Melting point 98°, DSC onset beginning at 136° C.

$^1$H NMR (d$_6$-dmso): 4.024 (singlet, relative area 3.067), 6.938 (singlet, relative area 1.661), 9.161 (singlet, relative area 0.932), 10.115 (singlet, relative area 1.000).

$^{13}$C NMR (d$_6$-dmso): 39.107 (singlet), 143.002 (singlet), 145.109 (singlet).

EXAMPLE 16

1-ethyl-4-amino-1,2,4-triazolium nitrocyanamide

To a preweighed Erlenmeyer flask, 3.1169 g, 16.1 mmol, of 1-ethyl-4-amino-1,2,4-triazolium bromide was measured out under nitrogen conditions. Methanol, 25 ml, was added to dissolve the salt, resulting in a clear solution, homogeneous. In a second preweighed Erlenmeyer flask, 3.0087 g, 15.5 mmol, of silver nitrocyanamide was measured out. Acetonitrile, 50 ml, was added along with 25 ml of methanol to dissolve the salt, resulting in a clear, homogeneous solution. The silver nitrocyanamide solution was added, dropwise, to the 1-ethyl-4-amino-1,2,4-triazolium bromide solution, resulting in an immediate clouding and precipitation in the solution. The reaction mixture was allowed to stir at ambient temperature for thirty minutes. At the end of the thirty minutes the reaction mixture was filtered through a filter set up (large 2-piece filter apparatus with the addition of filter paper and celite) removing the silver halide. The reaction vessel was rinsed three times, 20 ml each, with fresh methanol. The solution was transferred to a 500 ml round bottom flask, rinsing three times, 25 ml each, with fresh methanol. The flask was placed on a rotary evaporator, and the solvent was removed, leaving an oil. The oil was dissolved in a minimal amount of methanol and transferred to a preweighed Schlenk flask, placed in an oil bath at 60° C., and vacuum dried for 36-48 hours to leave a free flowing oil. Melting point 0° C.; DSC onset 175-180° C. Yield 3.1152 grams, 15.6 mmoles.

$^1$H NMR (d$_6$-dmso): 1.425, 1.444, 1.462 (triplet, relative area 3.019); 4.329, 4.347, 4.365, 4.383 (quartet, relative area 2.000); 6.849 (broad, relative area 1.819), 9.083 (singlet, relative area 0.943); 10.095 (singlet, relative area 0.956).

$^{13}$C NMR (d$_6$-dmso): 13.766 (singlet); 47.673 (singlet); 116.679, (singlet); 142.493 (singlet), 145.296 (singlet).

EXAMPLE 17

1-methylcyclopropyl-4-amino-1,2,4-triazolium nitrate

To a preweighed Erlenmeyer flask, 1.0303 g, 4.7 mmol, of 1-ethyl-4-amino-1,2,4-triazolium bromide was measured out under nitrogen conditions. Methanol, 25 ml, was added to dissolve the salt, resulting in a clear solution, homogeneous. In a second preweighed Erlenmeyer flask, 0.8045 g, 4.7 mmol, of silver nitrate was measured out. Acetonitrile, 4 ml, was added along with 15 ml of methanol to dissolve the salt, resulting in a clear, homogeneous solution. The silver nitrate solution was added, dropwise, to the 1-methylcyclopropyl-4-amino-1,2,4-triazolium bromide solution, resulting in an immediate clouding and precipitation in the solution. The reaction mixture was allowed to stir at ambient temperature for thirty minutes. At the end of the thirty minutes the reaction mixture was filtered through a filter of celite removing the silver halide. The reaction vessel was rinsed three times, 10 ml each, with fresh methanol and the solution transferred to a 500 ml round bottom flask. The flask was placed on a rotary evaporator, the solvent was removed, leaving an oil. The oil was dissolved in a minimal amount of methanol and transferred to a preweighed Schlenk flask, placed in an oil bath at 60° C., and vacuum dried for 24 hours. The product was an oil which solidified upon standing, yield 0.9285 grams, 4.7 mmoles. Melting point 53° C., DSC onset 210° C.

$^1$H NMR (d$_3$-CH$_3$CN): 0.411, 0.446, 0.457, 0.461, 0.469, 0.472, 0.484, 0.594, 0.613, 0.630, 0.641, 0.645, 0.650, 0.661, 0.665, 0.677, (complex multiplet of a doublet, relative area 4.000); 1.298, 1.305, 1.309, 1.317, 1.325, 1.329, 1.336, 1.344, 1.348, 1.356, 1.368 (broad multiplet, relative area 1.006), 4.181, 4.200 (doublet, relative area 2.001), 6.637 (broad singlet, relative area 2.001); 8.750 (singlet, relative area 0.890); 9.947 (singlet, relative area 0.930).

$^{13}$C NMR (d$_3$-CH$_3$CN): 4.615 (singlet); 10.528 (singlet); 58.173 (singlet); 143.507 (singlet), 146.083 (singlet).

EXAMPLE 18

1-methylcyclopropyl-4-amino-1,2,4-triazolium perchlorate

To a preweighed Erlenmeyer flask, 1.0385 g, 4.7 mmol, of 1-methylcyclopropyl-4-amino-1,2,4-triazolium bromide was measured out under nitrogen conditions. Methanol, 10 ml, was added to dissolve the salt, resulting in a clear solution, homogeneous. In a second preweighed Erlenmeyer flask, 0.9940 g, 4.7 mmol, of silver perchlorate was measured out. Acetonitrile, 4 ml, was added along with 5 ml of methanol to dissolve the salt, resulting in a clear, homogeneous solution. The silver perchlorate solution was added, dropwise, to the 1-methylcyclopropyl-4-amino-1,2,4-triazolium bromide solution, resulting in an immediate clouding and precipitation in the solution. The reaction mixture was allowed to stir at ambient temperature for thirty minutes. At the end of the thirty minutes the reaction mixture was filtered through a filter set up (large 2-piece filter apparatus with the addition of filter paper and celite) removing the silver halide. The reaction vessel was rinsed three times, 5 ml each, with fresh methanol. The solution was transferred to a 500 ml round bottom flask, rinsing three times, 5 ml each, with fresh methanol. The flask was placed on a rotary evaporator, and the solvent was removed, leaving an oil. The oil was dissolved in a minimal amount of methanol and transferred to a preweighed Schlenk flask, placed in an oil bath at 60° C., and vacuum dried for 24 hours. Product is a viscous oil. Melting point 0-5° C., DSC onset 225° C. Yield 1.310 grams, 4.7 mmoles.

$^1$H NMR (d$_6$-dmso): 0.463, 0.467, 0.475, 0.489, 0.558, 0.595, 0.605, 0.609, 0.614, 0.625, 0.640 (complex doublet, relative area 4.102), 1.286, 1.292, 1.304, 1.312, 1.316, 1.323, 1.331, 1.335, 1.343, 1.354 (broad complex singlet, relative area 0.960); 4.203, 4.221 (doublet, relative area 2.002); 6.888 (very broad, relative area 1.137), 9.163 (singlet, relative area 1.000); 10.143 (singlet, relative area 0.998).

$^{13}$C NMR (d$_6$-dmso): 3.926 (singlet); 10.007 (singlet); 56.495 (singlet); 142.315 (singlet), 145.307 (singlet).

EXAMPLE 19

1-methylcyclopropyl-4-amino-1,2,4-triazolium nitrocyanamide

To a preweighed Erlenmeyer flask, 1.0320 g, 4.7 mmol, of 1-methylcyclopropyl-4-amino-1,2,4-triazolium bromide was measured out under nitrogen conditions. Methanol, 10 ml, was added to dissolve the salt, resulting in a clear, homogeneous solution. In a second preweighed Erlenmeyer flask, 0.9122 g, 4.7 mmol, of silver nitrocyanamide was measured out. Acetonitrile, 5 ml, was added along with 10 ml of methanol to dissolve the salt, resulting in a clear, homogeneous solution. The silver nitrocyanamide solution was added, dropwise, to the 1-methylcyclopropyl-4-amino-1,2,4-triazolium bromide solution, resulting in an immediate clouding and precipitation in the solution. The reaction mixture was allowed to stir at ambient temperature for thirty minutes. At the end of the thirty minutes the reaction mixture was filtered through a filter set up (large 2-piece filter apparatus with the addition of filter paper and celite) removing the silver halide. The reaction vessel was rinsed three times, 5 ml each, with fresh methanol. The solution was transferred to a preweighed Schlenk flask, placed in an oil bath at 60° C., and vacuum dried for 24 hours, leaving a free flowing oil, 1.0499 grams, 4.7 mmoles. Melting point (−14)-(−10)° C.; DSC onset 200° C.

$^1$H NMR ($d_6$-dmso): 0.449, 0.461, 0.474, 0.551, 0.589, 0.599, 0.603, 0.608, 0.618, 0.634, (complex multiplet of a doublet, relative area 4.070); 1.271, 1.290, 1.301, 1.309, 1.320, 1.329, 1.339, 1.349, (broad multiplet, relative area 0.993), 4.202, 4.221 (doublet, relative area 2.010), 6.853 (broad singlet, relative area 2.001); 9.110 (singlet, relative area 1.000); 10.123 (singlet, relative area 0.997).

$^{13}$C NMR ($d_6$-dmso): 4.056 (singlet); 10.101 (singlet); 56.739 (singlet); 116.681, (singlet); 142.418 (singlet), 145.398 (singlet).

EXAMPLE 20

1-methyl-4-amino-1,2,4-triazolium nitrate

To a preweighed Erlenmeyer flask, 1.1726 grams, 5.18 mmoles of 1-methyl-4-amino-1,2,4-triazolium iodide was dissolved in twenty mL of fresh methanol and stirred vigorously with a Teflon stir bar. Silver nitrate, 0.8805 grams, 5.18 mmoles, was dissolved with 15 ml of methanol along with 3 ml of acetonitrile in a separate flask. The silver nitrate solution was added slowly to the vigorously stirred solution containing the 1-methyl-4-amino-1,2,4-triazolium iodide. After the addition of the silver nitrate solution was completed the reaction mixture was allowed to stir for 45 minutes more, then was filtered through a celite plug into a preweighed flask. The celite plug was washed with three five ml aliquots of fresh methanol. The filtrate flask was evacuated to leave a viscous oil which was then redissolved in 15 ml of fresh methanol and layered with 15 ml of diethyl ether, and subsequently placed in a refrigerator at 4° C. After 24 hours the filtrate solution was decanted away from the precipitated viscous oil, which was washed with three 10 ml aliquots of fresh diethyl ether and vacuum dried to a constant weight, 0.7936 g, 4.92 mmoles of 1-methyl-4-amino-1,2,4-triazolium nitrate. Melting point 54-56° C.; DSC onset 200° C.

$^1$H NMR ($d_6$-dmso): 4.051 (singlet); 6.991 (broad singlet); 9.079 (singlet); 10.116 (singlet).

$^{13}$C NMR ($d_6$-dmso): 39.208 (singlet); 143.584 (singlet); 145.615 (singlet).

EXAMPLE 21

1-methyl-4-amino-1,2,4-triazolium perchlorate 1.0596 g, 4.71 mmoles of 1-methyl-4-amino-1,2,4-triazolium iodide was dissolved into 20 ml of fresh methanol and stirred vigorously in an Erlenmeyer flask. Silver perchlorate, 0.9690 g, 4.70 mmoles was dissolved in 10 ml of fresh methanol in a separate flask. The silver perchlorate methanol solution was slowly added to the 1methyl-4-amino-1,2,4-triazolium iodide solution. The resultant solution was stirred for an additional 30 minutes and then was filtered through a celite plug into a preweighed flask. The filtrate solution was stripped down using high vacuum, to leave a crystalline solid of 1-methyl-4-amino-1,2,4-triazolium perchlorate, 0.8882 g, 4.50 mmoles. Melting point 80-83° C.; DSC onset 255° C.

$^1$H NMR ($d_6$-dmso): 4.020 (singlet); 6.891 (broad singlet); 9.090 (singlet); 10.008 (singlet).

$^{13}$C NMR ($d_6$-dmso): 39.016 (singlet); 143.066 (singlet); 145.125 (singlet).

EXAMPLE 22

1-methyl-4-amino-1,2,4-triazolium nitrocyanamide 0.8365 g, 3.70 mmoles of 1-methyl-4-amino-1,2,4-triazolium iodide was dissolved in 20 ml of ethanol in an Erlenmeyer flask and stirred vigorously with a Teflon stir bar. Silver nitrocyanamide, 0.7173 g, 3.6 mmoles, was dissolved in 5 ml of acetonitrile and 15 ml of methanol, in a separate flask and then slowly added to the stirred solution of 1-methyl-4-amino-1,2,4-triazolium iodide. The silver nitrocyanamide flask was washed with three 5 ml aliquots of fresh methanol and these washings were added to the reaction mixture, which was then stirred for an additional 45 minutes. The reaction mixture was filtered through a celite plug into a preweighed flask, with the celite plug being washed with three 5 ml aliquots of fresh methanol. The filtrate was stripped with high vacuum to leave the product 1-methyl-4-amino-1,2,4-triazolium nitrocyanamide as a free running oil, 0.4923 grams, 2.7 mmoles. Melting point 9-11° C.; DSC onset 180° C.

$^1$H NMR ($d_3$-CH$_3$CN): 4.058 (singlet, relative area 3.000), 6.186 (broad singlet, relative area 2.093), 8.663 (singlet, relative area 0.799), 9.515 (singlet, relative area 0.866).

$^{13}$C NMR ($d_3$-CH$_3$CN): 40.112 (singlet), 117.560 (singlet), 144.079 (singlet), 146.068 (singlet).

EXAMPLE 23

1-allyl-4-amino-1,2,4-triazolium nitrate 1-allyl-4-amino-1,2,4-triazolium bromide 1.0552 g, 5.16 mmoles, was added to a Erlenmeyer flask along with a Teflon stir bar and 10 ml of methanol, resulting in dissolution of the salt. In a separate flask, silver nitrate 0.8678 g, 5.10 mmoles, was weighed out and dissolved into 5 ml of methanol and 5 ml acetonitrile. The silver nitrate solution was then slowly added to the vigorously stirred solution of 1-allyl-4-amino-1,2,4-triazolium bromide and stirred at ambient temperature for one hour. The resultant solution was then filtered through a plug of celite into a preweighed Schlenk flask, with the precipitated silver bromide being washed with three aliquots, 5 ml each, of fresh methanol, and the resultant solution was removed with high vacuum over night. The resultant oil was redissolved into 5 ml of fresh methanol and layered with 15 ml of diethyl ether, and then placed in cold storage overnight. After 24 hours, an additional 20 ml of diethyl ether was added to insure complete precipitation of the product oil. The solution was then decanted away, and the product oil was washed with three aliquots, 25 ml each of cold diethyl ether and vacuum dried leaving 0.9799 g., 4.63 mmoles of 1-allyl-4-amino-1,2,4-triazolium nitrate. Melting point −15° C., DSC onset 140° C.

$^1$ H NMR ($d_3$-CD$_3$CN): 5.003, 5.0017 (doublet, relative area 2.076), 5.393, 5.419, 5.443 (multiplet, relative area 2.032), 5.992, 6.007, 6.017, 6.022, 6.032, 6.049, 6.060, 6.075, 6.091 (complex broad singlet, relative area 0.994), 6.750 (broad singlet, relative area 2.006), 8.845 (singlet, relative area 1.001), 10.025 (singlet, relative area 0.999).

$^{13}$C NMR (d$_3$-CD$_3$CN): 55.988 (singlet), 122.784 (singlet), 131.337 (singlet), 144.626 (singlet), 146.905 (singlet).

EXAMPLE 24

1-allyl-4-amino-1,2,4-triazolium perchlorate 1-allyl-4-amino-1,2,4-triazolium bromide 1.1478 g, 5.59 mmoles was weighed out and placed into an Erlenmeyer flask along with a Teflon stir bar and dissolved into 20 ml of methanol. Silver perchlorate, 1.1595 g, 5.59 mmoles, was weighed out in a separate flask and dissolved in 6 ml of fresh methanol. The silver perchlorate solution was then added slowly to the 1-allyl-4-amino-1,2,4-triazolium bromide solution, and the resultant mixture stirred at ambient temperature for one hour. At the end of this time the reaction solution was filtered through a celite plug to remove the silver bromide, into a pre-weighed Schlenk flask. The silver bromide was washed three times with 5 ml of fresh methanol, and the resultant solution was stripped under high vacuum over night, to leave a clear, free running oil of 1-allyl-4-amino-1,2,4-triazolium perchlorate, 1.1470 grams, 5.11 mmoles. Melting point (−11)-(0)° C.; DSC onset 180° C.

$^1$H NMR (d$_3$-CD$_3$CN): 4.975, 4.991 (doublet, relative area 2.618), 5.445, 5.457, 5.461, 5.463, 5.489, 5.491, 5.498 (complex multiplet, relative area 2.090), 6.011, 6.027, 6.037, 6.043, 6.053, 5.070, 6.080, 6.086, 6.096, 6.111 (complex singlet on top of broad singlet of NH$_2$, relative area 3.128), 8.658 (singlet, relative area 0.969), 9.428 (singlet, relative area 0.999).

$^{13}$C NMR (d$_3$-CD$_3$CN): 55.658 (singlet), 122.842 (singlet), 130.209 (singlet), 143.758 (singlet), 146.387 (singlet).

EXAMPLE 25

1-allyl-4-amino-1,2,4-triazolium nitrocyanamide 1-allyl-4-amino-1,2,4-triazolium bromide 0.9420 g, 4.59 mmoles, was added to a Erlenmeyer flask along with a Teflon stir bar and 15 ml of methanol, resulting in dissolution of the salt. In a separate flask, silver nitrocyanamide 0.8907 g, 4.59 mmoles, was weighed out and dissolved into 8 ml of methanol and 6 ml acetonitrile. The silver nitrocyanamide solution was then slowly added to the vigorously stirred solution of 1-allyl-4-amino-1,2,4-triazolium bromide and stirred at ambient temperature for one hour. The resultant solution was then filtered through a plug of celite into a pre-weighed Schlenk flask, with the precipitated silver bromide being washed with three aliquots, 5 ml each, of fresh methanol, and the resultant solution was removed with high vacuum over night to leave a free running oil of 1-allyl-4-amino-1,2,4-triazolium nitrocyanamide in high yield, 0.9433 grams, 4.46 mmoles. Melting point 15° C.; DSC onset 120° C.

$^1$H NMR (d$_3$-CD$_3$CN): 4.964, 4.984 (doublet, relative area 2.427), 5.416, 5.419, 5.433, 5.435, 5.469 (complex doublet, relative area 2.164), 6.191 (complex singlet on top of broad singlet of NH$_2$, relative area 3.128), 8.695 (singlet, relative area 0.961), 9.572 (singlet, relative area 1.000).

$^{13}$C NMR (d$_3$-CD$_3$CN): 55.698 (singlet), 117.700 (singlet), 122.762 (singlet), 130.275 (singlet), 143.810 (singlet), 146.370 (singlet).

EXAMPLE 26

1-allyl-4-amino-1,2,4-triazolium bromide 4-amino-1,2,4-triazole, 10.000 g, 118 mmoles, was dissolved into 200 ml of fresh acetonitrile and stirred vigorously. Allyl bromide, 43.10 g, 356 mmoles, was added slowly to the solution at room temperature. The reaction mixture was protected from light and allowed to stir for five days at ambient temperature, whereupon it was filtered, and transferred to a large round bottomed flask. The solvent and excess allyl bromide were rotary evaporated away leaving a viscous yellow oil. The oil was dissolved in a minimum amount of ethyl alcohol and the resultant clear, yellow solution layered with diethyl ether, and stored at 4° C. for 24 hours, resulting in a large crop of fine needles. The needles were filtered away washed with cold isopropyl alcohol and then cold diethyl ether, transferred to a preweighed Schlenk flask and vacuum dried overnight to leave a fluffy crystalline product of 1-allyl-4-amino-1,2,4-triazolium bromide in decent yield 12.657 g, 62 mmoles. Melting point: 59-62° C.; DSC onset: 130° C.

$^1$H NMR (d$_6$-dmso): 5.503 (broad singlet, relative area 2.130), 5.325, 5.359 (broad doublet, relative area 2.034), 5.994 (broad singlet, relative area 1.090), 7.079 (broad singlet, relative area 1.327), 9.242 (singlet, relative area 1.002), 10.372 (singlet, relative area 1.000).

$^{13}$C NMR (d$_6$-dmso): 53.865 (singlet), 121.031 (singlet), 130.488 (singlet), 142.857 (singlet), 145.504 (singlet).

The above examples demonstrate the facile nature of the new invention, but are not limited to the above said reagents and materials. It can easily be observed by one skilled in the art that simple substitutions of the cation used in the energetic salt metathesis (aforementioned reaction 2) could be used, based mainly on solubilities of the resultant salts, whereby the corresponding formed halide salt of the cation would have little or no solubility in the reaction medium, making separation of the product from the simple halide salt easy. The resultant salts have many possibilities in their utility, most namely that as energetic ingredients to be used as materials in liquid propellant materials whether it be in a monopropellant scenario or as a fuel or oxidizer in a bipropellant scenario. The intermediates, namely the halide salts of 1-substituted-4-amino-1,2,4-triazole can be very useful intermediates in the syntheses of many triazole based systems, since only the one position, namely the number one nitrogen atom of the 1,2,4-triazole ring system is substituted in high yield and purity. The new invention is a marked improvement over the literature preparatory route (see Scriven, Keay, Goe, and Astleford in *J. Org. Chem.* 1989, 54, 731) which uses only a one to one ratio of reactants (alkyl bromides), or uses chloroalkanes which are much less reactive, both of which lead to contamination of the final product with the starting material 4-amino-1,2,4-triazole, making separation difficult.

Thus the invention provides an improved synthesis route to 1-substituted 4-amino-1,2,4-triazolium halide salts by reacting excess organic substituted halide, where excess organic substituted halide is n>2 and most useful from 2 to 5 mole equivalents of organic substituted halide with 4-amino-1,2,4-triazole, which results in high purity, high yield of the desired products in polar solvents at temperatures under 100° C., e.g., ranging from ambient temperature to about 80° C. The new route allows for easy separation of the 1-organic substituted-4-amino-1,2,4-triazolium halide salts in high yield and purity.

The invention also provides for the formation of new ionic liquids based upon 1-substituted-4-amino-1,2,4-triazolium salts, including a new class of ionic liquids where the anion can be chosen from several energetic species found in readily available salts to yield 1-substituted-4-amino-1,2,4-triazolium energetic salts in high yield and purity.

Accordingly, a new family of salts has been synthesized in high yield and purity from commercially available starting materials. 1-substituted-4-amino-1,2,4-triazolium salts have been synthesized through the reaction of n moles (n>2) of an organic halide material with 4-amino-1,2,4-triazole in polar solvents such as acetonitrile or isopropyl alcohol. The new 1-substituted-4-amino-1,2,4-triazolium salts (halide salts) are covered in high yields as well as in high purity, with no contamination evident from the starting materials. The new 1-substituted-4-amino-1,2,4-triazolium halide salts are crystalline materials with melting points below 100° C. These 1-substituted-4-amino-1,2,4-triazolium halide salts can be reacted cleanly with silver salts of energetic anions, such as nitrate, perchlorate & nitrocyanamide, to yield highly energetic, low melting 1-substituted-4-amino-1,2,4-triazolium salts in high yields and high purities, which are easily separated from the reaction mixture. These new salts have high thermal stability and should have application as new fuels, monopropellants, electrolytes, gun propellants, and gas generators.

Also, these new salts can be used as propellant ingredients, low melting casting agents for explosives and warheads, monopropellant ingredients, gun propellants, plasticizers for explosives and propellants, in mixtures with other well known energetic materials including, ammonium nitrate, ammonium perchlorate, ammonium dinitramide hydroxylammonium nitrate (HAN), hydrolylammonium perchlorate, hydroxylammonium dinitramide (HADN) and hydrazinium nitrate. These new materials can have application as new electrolytes for batteries for military applications.

Commercial applications of the inventive salts are similar to the uses listed above. Also, these salts, most notably the halide salts of 1-substituted-4-amino-1,2,4-triazolium cations, are excellent synthons for certain triazoles used in the pharmaceutical industry, as the nitrogen in position 1 of the 1,2,4-triazole ring is substituted cleanly, in high yield and purity, without contamination from the starting materials and can be recovered as a highly crystalline salt.

The invention claimed is:

1. A method for making energetic ionic salts comprising the reaction:

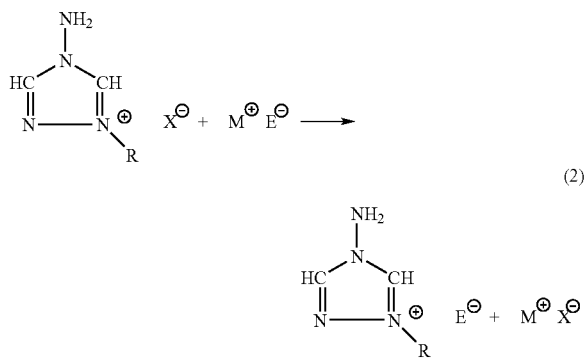

(2)

where X is selected from the group consisting of bromine, chlorine, iodine and substituted sulfate —S(=O)$_2$—R$_1$ where R$_1$ is selected from the group consisting of alkyl, phenyl, substituted phenyl, trifluoromethyl (CF$_3$) and nitratato (ONO$_2^-$)—;

and the M+ cation is selected from the group consisting of silver (Ag$^+$), potassium (K$^+$), sodium (Na$^+$), Strontium (Sr$^+$), cesium (Cs$^+$), ammonium (NH$_4^+$) and substituted ammonium NRR'R''R'''+ (where R, R', R'', R''' can be equivalent or all different with some but not all pendant R groups being hydrogen atoms, while the other R, R', R'', and R''' are substituted alkyl chains from C$_1$-C$_{20}$ and these substituted R groups are substituted straight, branched, cyclic, unsaturated or joined together as well as in chains containing nitrogen or oxygen, and wherein the E anion is selected from the group consisting of nitrate (NO$_3^+$), perchlorate (ClO$_{4-}$), dinitramide (N(NO$_2$)$_2^+$), nitroformate (C(NO$_2$)$_3^+$), nitrocyanamide N(NO$_2$)(CN)$^-$, dicyanamide (N(CN)$_2^-$), 5-nitro-1,2,3,4-tetrazoloate, 3-nitro-1,2,4-triazolate, 3,5-dinitro-1,2,4-triazolate, 2,4,5-trinitro-1,3-imidazolate, bitetrazolate, bitetrazolylamide, perchlorylamide (N—ClO$_3^{-2}$), 2-oxo-5-nitro-1,2,3,4-tetrazolate and 1-oxo-3,5-dinitro-1,2,4-triazolate.

2. The method of claim 1 conducted in a polar solvent.

3. Energetic ionic salts selected from the group consisting of 1-methyl-4-amino-1,2,4-triazolium nitrate, 1-methyl-4-amino-1,2,4-triazolium perchlorate, 1-methyl-4-amino-1,2,4-triazolium nitrocyanamide, 1-ethyl-4-amino-1,2,4-triazolium nitrate, 1-ethyl-4-amino-1,2,4-triazolium perchlorate, 1-ethyl-4-amino-1,2,4-triazolium nitrocyanamide, 1-ethanol-4-amino-1,2,4-triazolium nitrate, 1-ethanol-4-amino-1,2,4-triazolium perchlorate, 1-ethanol-4-amino-1,2,4-triazolium nitrocyanamide, 1-n-propyl-4-amino-1,2,4-triazolium nitrate, 1-n-propyl-4-amino-1,2,4-triazolium perchlorate, 1-n-propyl-4-amino-1,2,4-triazolium nitrocyanamide, 1-n-butyl-4-amino-1,2,4-triazolium perchlorate, 1-n-butyl-4-amino-1,2,4-triazolium nitrocyanamide, 1-methylcyclopropyl-4-amino-1,2,4-triazolium nitrate, 1-methylcyclopropyl-4-amino-1,2,4-triazolium perchlorate, 1-methylcyclopropyl-4-amino-1,2,4-triazolium nitrocyanamide, 1-(2-propenyl)-4-amino-1,2,4-triazolium nitrate, 1-(2-propenyl)-4-amino-1,2,4-triazolium perchlorate and 1-(2-propenyl)-4-amino-1,2,4-triazolium nitrocyanamide.

4. The salts of claim 3 having melting points below 100° C.

5. The method of using 1-substituted-4-amino-1,2,4-triazolium salts as energetic ingredients wherein said 1-substituted is selected from the group consisting of 1-methyl, 1-ethyl, 1-ethanol, 1-n-propyl, 1-n-butyl, 1-methylcyclopropyl- and 1(2-propenyl), by adding or mixing same solely or with other ingredients, for propellants, fuels, explosives or as admixtures therewith.

* * * * *

UNITED STATES PATENT AND TRADEMARK OFFICE
CERTIFICATE OF CORRECTION

PATENT NO. : 7,745,635 B1
APPLICATION NO. : 10/465836
DATED : June 29, 2010
INVENTOR(S) : Greg W. Drake et al.

It is certified that error appears in the above-identified patent and that said Letters Patent is hereby corrected as shown below:

On the Title Pg. item (74), "William J. O'Brien" should read -- Thomas C. Stover --.

Signed and Sealed this

Fifth Day of October, 2010

David J. Kappos
*Director of the United States Patent and Trademark Office*